(12) United States Patent
Maskara et al.

(10) Patent No.: US 7,904,156 B2
(45) Date of Patent: Mar. 8, 2011

(54) MODULATION OF AV DELAY TO CONTROL VENTRICULAR INTERVAL VARIABILITY

(75) Inventors: Barun Maskara, Blaine, MN (US); Donald L. Hopper, Maple Grove, MN (US); Yinghong Yu, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 786 days.

(21) Appl. No.: 11/894,081

(22) Filed: Aug. 20, 2007

(65) Prior Publication Data

US 2009/0054944 A1    Feb. 26, 2009

(51) Int. Cl.
A61N 1/362 (2006.01)
A61N 1/365 (2006.01)

(52) U.S. Cl. .............................. 607/9; 607/17
(58) Field of Classification Search ............ 607/9, 14, 607/17
See application file for complete search history.

(56) References Cited

U.S. PATENT DOCUMENTS

| | | |
|---|---|---|
| 4,674,518 A | 6/1987 | Salo |
| 4,686,987 A | 8/1987 | Salo |
| 5,086,774 A | 2/1992 | Duncan |
| 5,334,222 A | 8/1994 | Salo |
| 5,417,717 A | 5/1995 | Salo |
| 5,466,245 A | 11/1995 | Spinelli |
| 5,487,752 A | 1/1996 | Salo et al. |
| 5,601,613 A * | 2/1997 | Florio et al. ............... 607/14 |
| 5,626,623 A | 5/1997 | Kieval et al. |
| 5,700,417 A | 12/1997 | Fernyhough |
| 5,800,464 A | 9/1998 | Kieval |
| 6,141,590 A | 10/2000 | Renirie |
| 6,144,800 A | 11/2000 | Kobayashi |
| 6,144,880 A | 11/2000 | Ding |
| 6,221,011 B1 | 4/2001 | Bardy |
| 6,270,457 B1 | 8/2001 | Bardy |
| 6,277,072 B1 | 8/2001 | Bardy |
| 6,280,380 B1 | 8/2001 | Bardy |
| 6,312,378 B1 | 11/2001 | Bardy |
| 6,336,903 B1 | 1/2002 | Bardy |
| 6,358,203 B2 | 3/2002 | Bardy |
| 6,368,284 B1 | 4/2002 | Bardy |
| 6,371,922 B1 | 4/2002 | Baumann |
| 6,398,728 B1 | 6/2002 | Bardy |
| 6,440,066 B1 | 8/2002 | Bardy |
| 6,640,135 B1 | 10/2003 | Salo et al. |
| 6,748,271 B2 | 6/2004 | Spinelli et al. |
| 6,871,088 B2 | 3/2005 | Chinchoy |
| 6,985,772 B2 | 1/2006 | Holmstrom et al. |
| 7,027,866 B2 | 4/2006 | Warkentin |

(Continued)

OTHER PUBLICATIONS

Office Action dated Aug. 6, 2009 from U.S. Appl. No. 11/799,794.

(Continued)

*Primary Examiner* — Carl H. Layno
*Assistant Examiner* — Jon-Eric C. Morales
(74) *Attorney, Agent, or Firm* — Hollingsworth & Funk, LLC

(57) ABSTRACT

System and methods provide pacing therapy that modulates the atrioventricular (AV) delay to control ventricular interval variability. A base AV delay is determined as a function of heart rate. For each cardiac cycle, the base AV delay is modulated to reduce beat-to-beat variability of successive ventricular beats. The modulated AV delay compensates for variability of successive atrial beats. For example, modulation of the base AV delay may involve varying the AV delay inversely with a change in atrial interval.

19 Claims, 12 Drawing Sheets

U.S. PATENT DOCUMENTS

| | | |
|---|---|---|
| 7,107,093 B2 | 9/2006 | Burnes |
| 7,139,608 B2 | 11/2006 | Ideker et al. |
| 7,181,285 B2 | 2/2007 | Lindh |
| 7,215,998 B2 | 5/2007 | Wesselink et al. |
| 7,302,295 B2 | 11/2007 | Stahmann et al. |
| 7,343,199 B2 | 3/2008 | Hatlestad et al. |
| 2002/0082646 A1* | 6/2002 | Casavant et al. ............ 607/9 |
| 2003/0040777 A1 | 2/2003 | Shemer et al. |
| 2003/0045909 A1 | 3/2003 | Gross et al. |
| 2005/0027322 A1 | 2/2005 | Warkentin |
| 2005/0027323 A1 | 2/2005 | Mulligan et al. |
| 2005/0038479 A1 | 2/2005 | Deno et al. |
| 2005/0109338 A1 | 5/2005 | Stahmann |
| 2005/0234517 A1 | 10/2005 | Braunschweig et al. |
| 2006/0173493 A1 | 8/2006 | Armstrong et al. |
| 2006/0247702 A1* | 11/2006 | Stegemann et al. ........ 607/17 |
| 2007/0060959 A1 | 3/2007 | Salo et al. |
| 2007/0293897 A1 | 12/2007 | Sheldon et al. |

OTHER PUBLICATIONS

U.S. Office Action dated Apr. 27, 2009 from U.S. Appl. No. 11/799,794, 6 pages.
U.S. Office Action dated Aug. 6, 2009 from U.S. Appl. No. 11/799,794, 23 pages.
Dec. 27, 2009, U.S. Office Action dated Apr. 27, 2009 from U.S. Appl. No. 11/799,794, 24 pages.
U.S. Office Action dated Jun. 29, 2009 from U.S. Appl. No. 11/799,794, 6 pages.
U.S. Office Action dated Nov. 5, 2009 from U.S. Appl. No. 11/799,794, 11 pages.
U.S. Office Action dated Feb. 10, 2010 from U.S. Appl. No. 11/799,794, 11 pages.
U.S. Office Action dated Feb. 24, 2010 from U.S. Appl. No. 11/799,794, 16 pages.
U.S. Office Action dated Mar. 22, 2010 from U.S. Appl. No. 11/894,082, 7 pages.
International Search Report and Written Opinion dated Nov. 17, 2008 from International Application No. PCT/US2008/009612, 15 pages.
International Preliminary Report on Patentability dated Mar. 4, 2010 from International Application No. PCT/US2008/009612, 10 pages.
Ogoh et al., "Cardiopulmonary Baroreflex is Reset During Dynamic Exercise", J. Appl Physiol, 100, 2006, pp. 51-59.
Nakamoto et al., "Beat-to-Beat Modulation of Atrioventricular Conduction during Dynamic Exercise in Humans", Japanese Journal of Physiology, vol. 55, 2005, pp. 37-51.
Office Action Response submitted May 14, 2010 to office Action dated Feb. 24, 2010 from U.S. Appl. No. 11/799,794, 10 pages.
Restriction Response submitted Apr. 21, 2010 to restriction dated Mar. 22, 2010 from U.S. Appl. No. 11/894,082, 5 pages.
Office Action dated May 12, 2010 from U.S. Appl. No. 11/894,082, 16 pages.
Examiner Interview Summary dated Aug. 18, 2010 from U.S. Appl. No. 11/799,794, 4 pages.
Office Action dated Aug. 26, 2010 from U.S. Appl. No. 11/799,794, 12 pages.
Office Action Response dated Aug. 12, 2010 to office action dated May 12, 2010 from U.S. Appl. No. 11/894,082, 8 pages.
Office Action dated Jun. 16, 2010 from U.S. Appl. No. 11/799,794, 15 pages.
Examiner Interview Summary dated Oct. 27, 2010 from U.S. Appl. No. 11/799,794, 3 pages.
Office Action Response dated Oct. 26, 2010 from U.S. Appl. No. 11/799,794, 9pages.
Office Action dated Nov. 15, 2010 from U.S. Appl. No. 11/799,794, 3 pages.

* cited by examiner

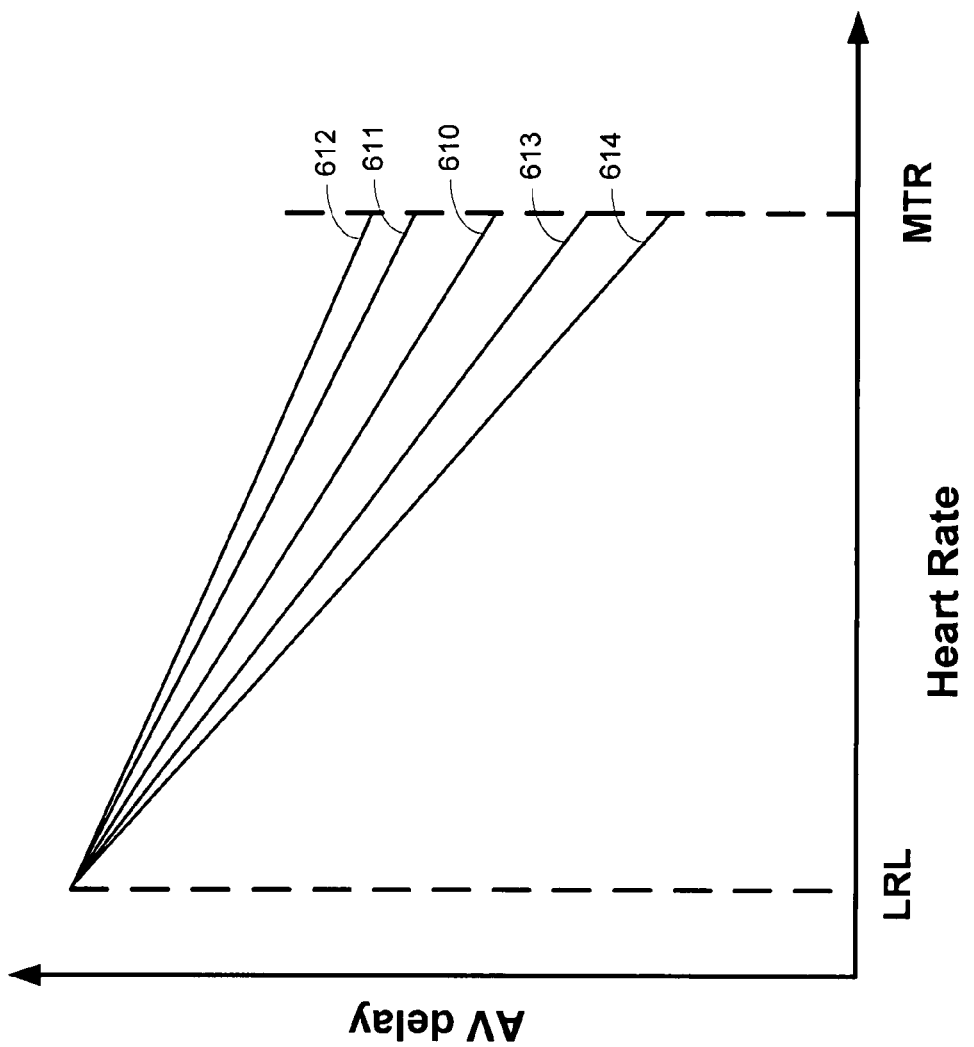

MODULATION OF AV DELAY TO CONTROL VENTRICULAR INTERVAL VARIABILITY

FIELD OF THE INVENTION

The present invention relates generally to cardiac pacing therapy, and more specifically, to control of ventricular interval variability through modulation of the atrioventricular delay.

BACKGROUND OF THE INVENTION

When functioning normally, the heart produces rhythmic contractions and is capable of pumping blood throughout the body. The heart has specialized conduction pathways in both the atria and the ventricles that enable the rapid conduction of excitation impulses (i.e. depolarizations) from the sinoatrial (SA) node throughout the myocardium. These specialized conduction pathways conduct the depolarizations from the SA node to the atrial myocardium, to the atrio-ventricular node, and to the ventricular myocardium to produce a coordinated contraction of both atria and both ventricles.

The conduction pathways synchronize the contractions of the muscle fibers of each chamber as well as the contraction of each atrium or ventricle with the opposite atrium or ventricle. Without the timing and synchronization afforded by the normally functioning specialized conduction pathways, the heart's pumping efficiency is greatly diminished. Patients who exhibit pathology of these conduction pathways can suffer compromised cardiac output.

Cardiac rhythm management devices have been developed that provide pacing stimulation to one or more heart chambers in an attempt to improve the rhythm and coordination of atrial and/or ventricular contractions. Cardiac rhythm management devices typically include circuitry to sense signals from the heart and a pulse generator for providing electrical stimulation to the heart. Leads extending into the patient's heart chamber and/or into veins of the heart are coupled to electrodes that sense the heart's electrical signals and for delivering stimulation to the heart in accordance with various therapies for treating cardiac arrhythmias.

Pacemakers are cardiac rhythm management devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

Pacing therapy has been used in the treatment of heart failure (HF). HF causes diminished pumping power of the heart, resulting in the inability to deliver enough blood to meet the demands of peripheral tissues. HF may cause weakness, loss of breath, and build up of fluids in the lungs and other body tissues. HF may affect the left heart, right heart or both sides of the heart. For example, HF may occur when deterioration of the muscles of the heart produce an enlargement of the heart and/or reduced contractility. The reduced contractility decreases the cardiac output of blood and may result in an increased heart rate. In some cases, HF is caused by unsynchronized contractions of the left and right heart chambers, denoted atrial or ventricular dysynchrony. Particularly when the left or right ventricles are affected, the unsynchronized contractions can significantly decrease the pumping efficiency of the heart.

Pacing therapy to promote synchronization of heart chamber contractions to improve cardiac function is generally referred to as cardiac resynchronization therapy (CRT). Some cardiac pacemakers are capable of delivering CRT by pacing multiple heart chambers. Pacing pulses are delivered to the heart chambers in a sequence that causes the heart chambers to contract in synchrony, increasing the pumping power of the heart and delivering more blood to the peripheral tissues of the body. In the case of dysynchrony of right and left ventricular contractions, a biventricular pacing therapy may pace one or both ventricles. Bi-atrial pacing or pacing of all four heart chambers may alternatively be used.

SUMMARY OF THE INVENTION

The present invention is directed to pacing therapy systems and methods that provide modulation of the atrioventricular (AV) delay to control ventricular interval variability. One embodiment of the invention is directed to a method of delivering pacing therapy to a heart. A base AV delay is determined as a function of heart rate. For each cardiac cycle, the base AV delay is modulated to reduce beat-to-beat variability of successive ventricular beats. The modulated AV delay compensates for variability of successive atrial beats. For example, modulation of the base AV delay may involve varying the AV delay inversely with a change in atrial interval.

According to one aspect, determining the base AV delay involves selecting a base AV delay function from a plurality of possible functions. One or more additional AV delay modulation parameters may also be selected. In some configurations, one or both of selecting the base AV delay function and selecting the additional AV delay modulation parameters are performed by a human analyst. In some configurations, one or both of selecting the base AV delay and selecting the additional AV delay modulation parameters are performed algorithmically by a cardiac device.

Modulation of the base AV delay may be determined using an AV delay of a previous cardiac cycle, a ventricular interval of a previous cardiac cycle, and an atrial interval of a current cardiac cycle. The base AV delay may be modulated according to a modulation index which is associated with a range of AV delay modulation that varies as a function of heart rate. In some implementations, AV delay modulation begins after the heart rate exceeds a threshold value.

The method may include a enabling an AV interval data collection mode of the cardiac device. The AV interval data collection mode allows data related to a relationship between heart rate and intrinsic AV interval to be collected via the cardiac device. The collected data may be used to determine one or more parameters of AV delay modulation, such as the base AV delay, the modulation index and/or a threshold for AV delay modulation.

Another embodiment of the invention involves a cardiac rhythm management system. The system includes electrodes electrically coupled to a heart. A therapy controller is configured to determine a base AV delay as a function of heart rate. For each cardiac cycle, the base AV delay is modulated by the therapy controller to reduce beat-to-beat variability in ventricular intervals. A pacing therapy delivery circuit delivers pacing therapy via the electrodes using the modulated AV delay. For example, the therapy controller may be configured to modulate the base AV delay inversely with a change in atrial interval for each cardiac cycle.

The system may include an external device configured to facilitate selection by a physician of one or more of a base AV delay function and additional AV delay modulation parameters. The therapy controller determines the base AV delay using the selected AV delay function and/or the selected additional AV delay modulation parameters.

In certain configurations, the therapy controller is configured to algorithmically select one or more of a base AV delay function and additional AV delay modulation parameters. In this configuration, the therapy controller determines the base AV delay using the algorithmically selected AV delay function and/or the selected additional AV delay modulation parameters.

The therapy controller may modulate the base AV delay for the cardiac cycle in various ways. In one example, the base AV delay is modulated based on an AV delay of a previous cardiac cycle, a ventricular interval of a previous cardiac cycle, and an atrial interval of the cardiac cycle. The therapy controller may be configured to collect data related to a relationship between heart rate and intrinsic AV interval. The therapy controller determines one or more parameters of AV delay modulation using the collected data.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 6A illustrates several linear AV delay modulation functions providing differing slopes for AV delay vs. heart rate that may be selected in accordance with embodiments of the invention;

Figure 1:
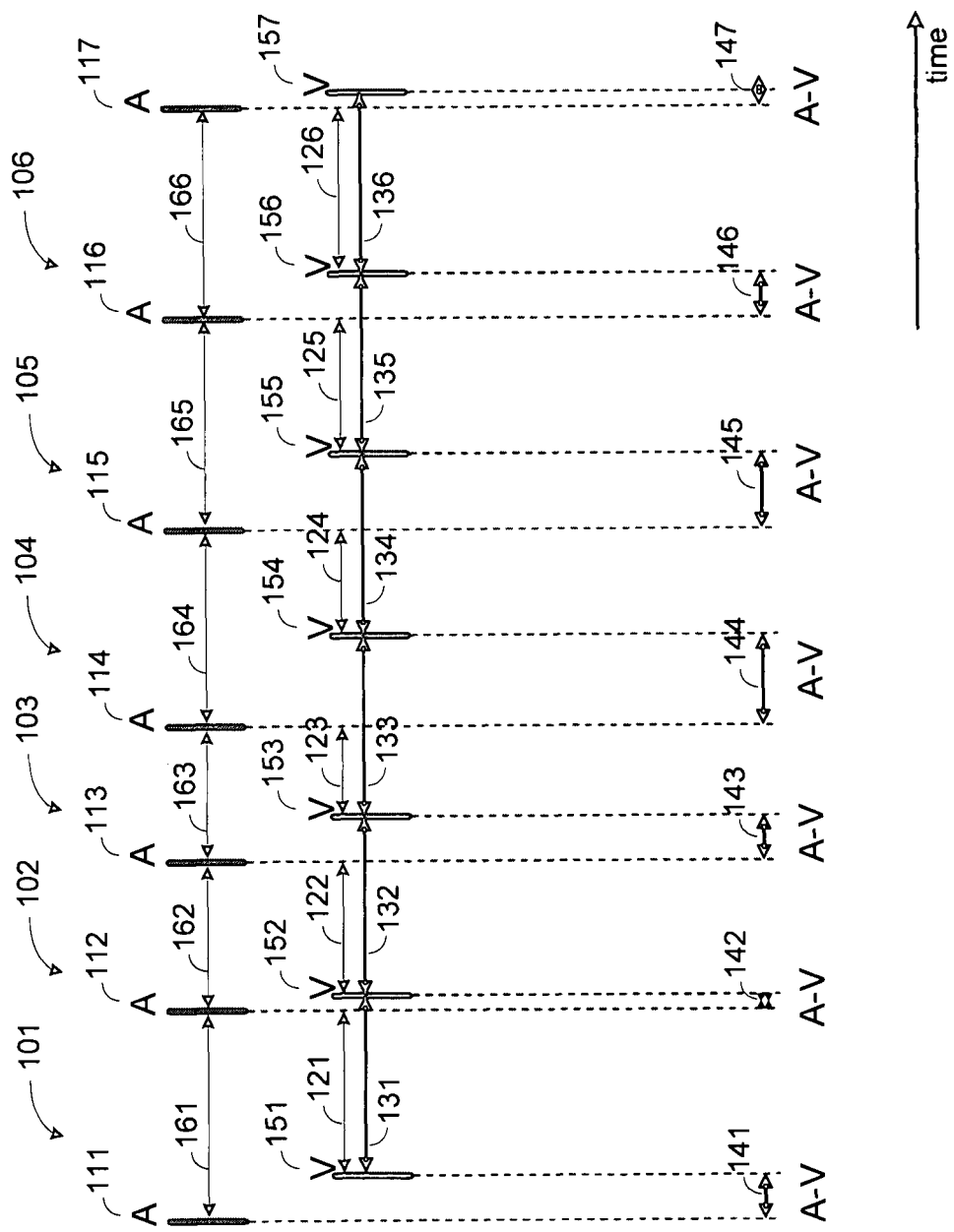
FIG. 1 is a timing diagram that illustrates modulation of the AV delay in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described hereinbelow. For example, a device or system may be implemented to include one or more of the advantageous features and/or processes described below. It is intended that a device or system need not include all of the features described herein, but may be implemented to include selected features that provide for useful structures and/or functionality. Such a device or system may be implemented to provide a variety of therapeutic or diagnostic functions.

Recent studies show that during exercise the intrinsic variability of the atrial (P-P) and ventricular (R-R) intervals decreases, with the decrease in the variability of the R-R being most pronounced, especially at higher heart rates of about 140-160 bpm. Conversely, variability of the intrinsic atrioventricular (P-R) interval and the change in P-R interval variability increases during exercise. The conclusion drawn from these studies is that at elevated heart rates the AV nodal mechanism functions to produce P-R intervals that cancel fluctuations in the P-P intervals within one beat, thus decreasing the variability of R-R intervals. (See e.g., "Variability of Ventricular Excitation Interval does not Reflect Fluctuation in Atrial Excitation Interval during Exercise in Humans: AV Nodal Function as Stabilizer," J. Physiol. Sci. Vol. 56, No. 1, February 2006, pp. 67-77).

As exertion increases from a resting level, stroke volume typically increases and then gradually plateaus. Stroke volume is increased through a number of mechanisms, including increased ventricular preload, decreased ventricular afterload, and increased myocardial contractility. At high levels of exertion, stroke volume remains relatively constant and additional cardiac output is achieved through increased heart rate.

The intrinsic variability of the P-R intervals operates to stabilize beat to beat stroke volume. For example, if stroke volume decreases as a result of decreased preload, the AV node operates to elongate the P-R interval and shorten the P-P interval whereas if stroke volume increases due to increased preload, the P-R interval is shortened and the P-P interval is elongated. This effect is especially pronounced during ventilation cycles.

Embodiments of the invention are directed to cardiac rhythm management devices, systems and methods that provide beat to beat modulation of AV timing intervals to produce physiologic pacing as heart rate increases above the lower rate limit of the device. Modulation of the AV timing intervals provides a reduction in ventricular interval variation, thus stabilizing stroke volume. The approaches described herein provide for modulation of the AV delay for each cardiac cycle.

The modulation of the AV delay counteracts variability of the intrinsic or paced atrial intervals and reduces ventricular interval variability. The approaches of the invention involve adjusting the AV delay between a sensed or paced atrial beat of a cardiac cycle and a paced ventricular beat for the cardiac cycle.

The timing diagram of FIG. 1 illustrates modulation of the AV delay in accordance with embodiments of the invention. The six cardiac cycles 101-106 of FIG. 1 may be conceptually visualized as beginning with an evoked or intrinsic atrial depolarization 111-116 and continuing until the evoked or intrinsic atrial depolarization 112-117 initiating the next cycle. The cardiac cycles may be visualized as comprising an AV delay 141-147 which is the interval between atrial and ventricular beats of the cardiac cycle followed by a VA delay 121-126 which is the interval between the ventricular beat 151-156 of a cardiac cycle and the atrial beat 112-117 of the next cardiac cycle. As previously discussed, physiologic pacing as heart rate increases toward a maximum tracking rate (MTR) involves reducing the variability in ventricular intervals 131-136 with increasing heart rate. The ventricular intervals 131-136 illustrated in FIG. 1 begin with the ventricular beat 151-156 of a first cardiac cycle and end with a ventricular beat 152-157 of the next successive cardiac cycle.

In atrial tracking mode, after sensing an intrinsic atrial depolarization, the cardiac rhythm management system initiates an AV delay. According to embodiments of the invention, modulation of the AV delay 141-147 of each cardiac cycle 111-117 compensates for variability of the A-A intervals 161-166 and reduces variability in the V-V intervals 131-136.

Figure 2:
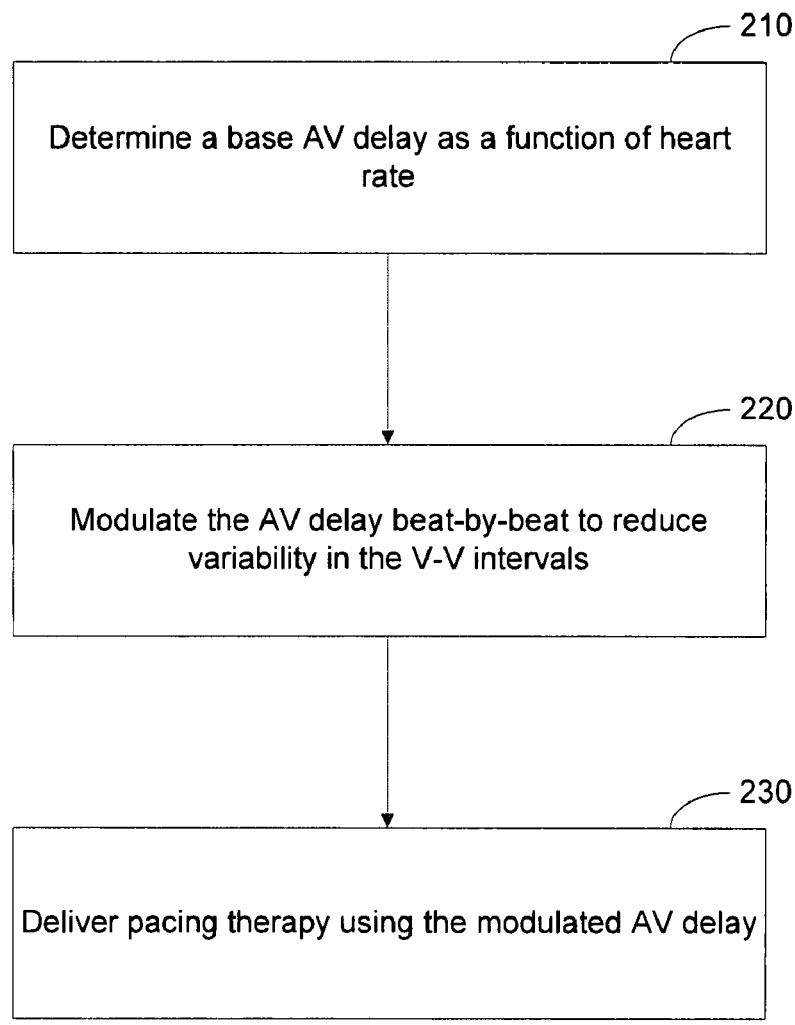
FIG. 2 is a flow diagram that illustrates delivery of pacing therapy with AV delay modulation in accordance with embodiments of the invention.
Figure 3:
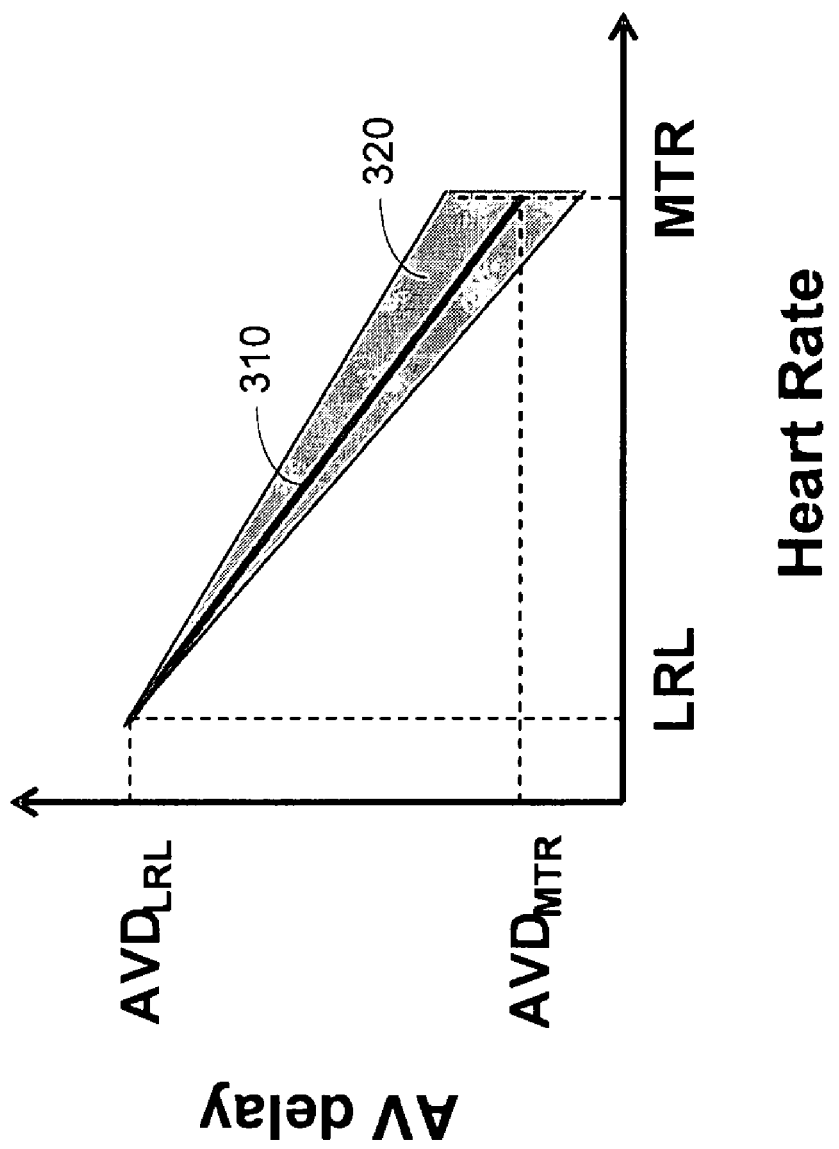
FIG. 3 illustrates a base AV delay that decreases as a linear function of heart rate in accordance with embodiments of the invention.

FIG. 2 is a flow diagram that illustrates delivery of pacing therapy with AV delay modulation in accordance with embodiments of the invention. In one embodiment, a base AV delay is determined 210 as a function of heart rate. For example, FIG. 3 illustrates a base AV delay 310 that decreases as a linear function of heart rate. The base AV delay 310 decreases from a first AV delay, $AVD_{LRL}$ at the a lower rate pacing limit (LRL) to a second AV delay, $AVD_{MTR}$ at a maximum tracking rate (MTR). The base AV delay may be selected to facilitate cardiac resynchronization therapy by promoting consistent ventricular pacing and/or may be selected to avoid fusion beats and/or may be selected to provide rate adaptive pacing and/or may be selected to provide or promote some other aspect of a prescribed pacing therapy. The AV delay modulation techniques discussed herein are particularly useful when applied in VDD, DDD, or DDDR pacing modes to stabilize V-V intervals at elevated heart rates.

Figure 4:
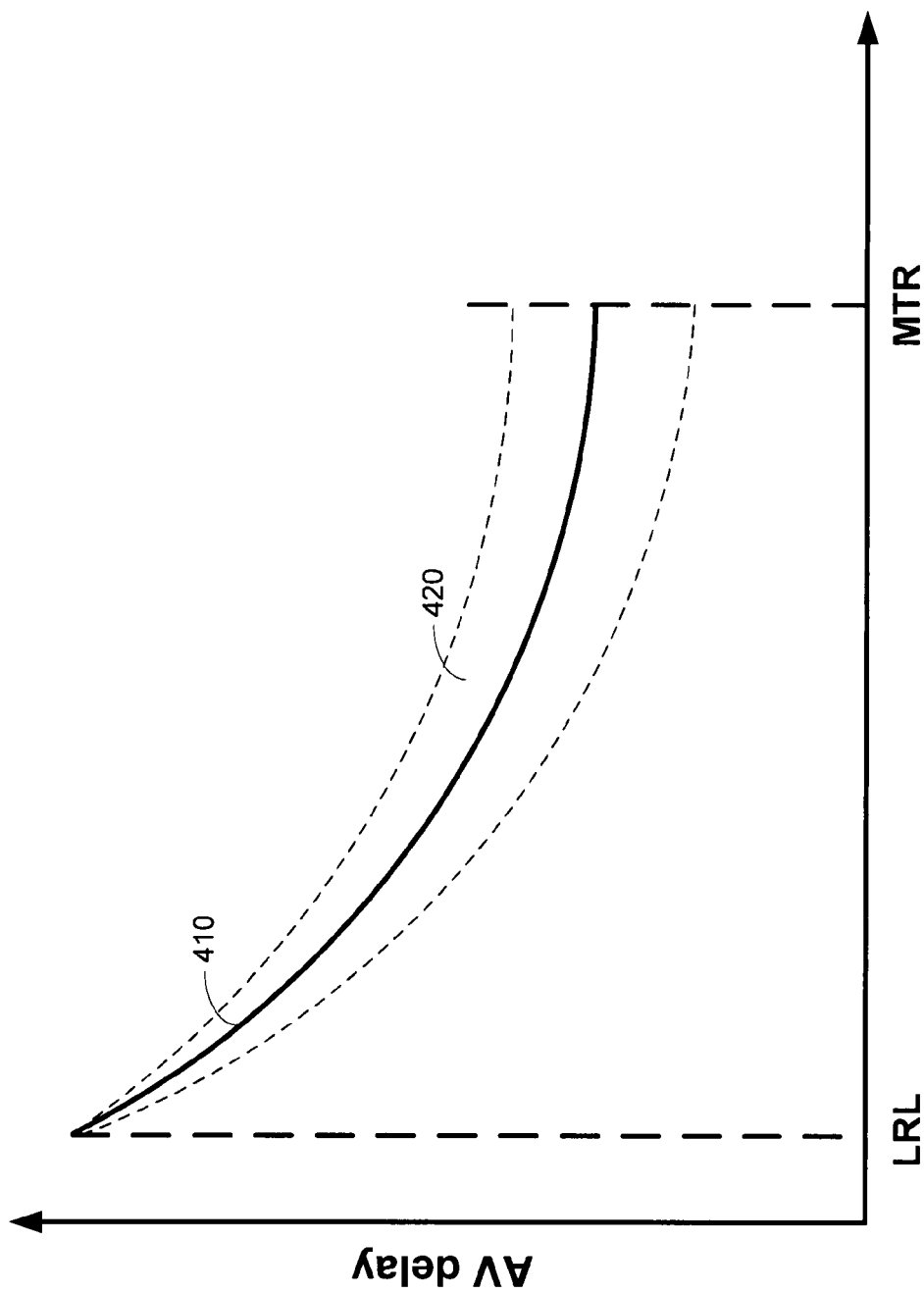
FIG. 4 illustrates a base AV delay that decreases as a non-linear function of heart rate in accordance with embodiments of the invention.

The base AV delay is modulated 220 beat by beat. The modulation of the AV delay compensates for variability in the A-A intervals to reduce variability in V-V intervals. Pacing therapy is delivered 230 using the modulated AV delay. FIG. 3 illustrates one example of a range 320 for AV delay modulation when the base AV delay 310 varies linearly with heart rate. In this example, the range 320 of AV delay modulation about the base AV delay 310 increases from substantially zero modulation at the LRL to the greatest range of modulation at the MTR. For each cardiac cycle, the amount of AV delay modulation depends on the heart rate and the length of the A-A interval. The V-V interval stability is enhanced by modulating the AV interval inversely with each change in the A-A interval. In some implementations, both the base AV delay 310 and/or the variation in the amount of modulation of the base AV delay may be linear functions of heart rate, as illustrated in FIG. 3. In other implementations, illustrated in FIG. 4, one or both of the base AV delay 410 and functions defining the modulation range 420 of the base AV delay may be non-linear functions of heart rate.

Figure 5:
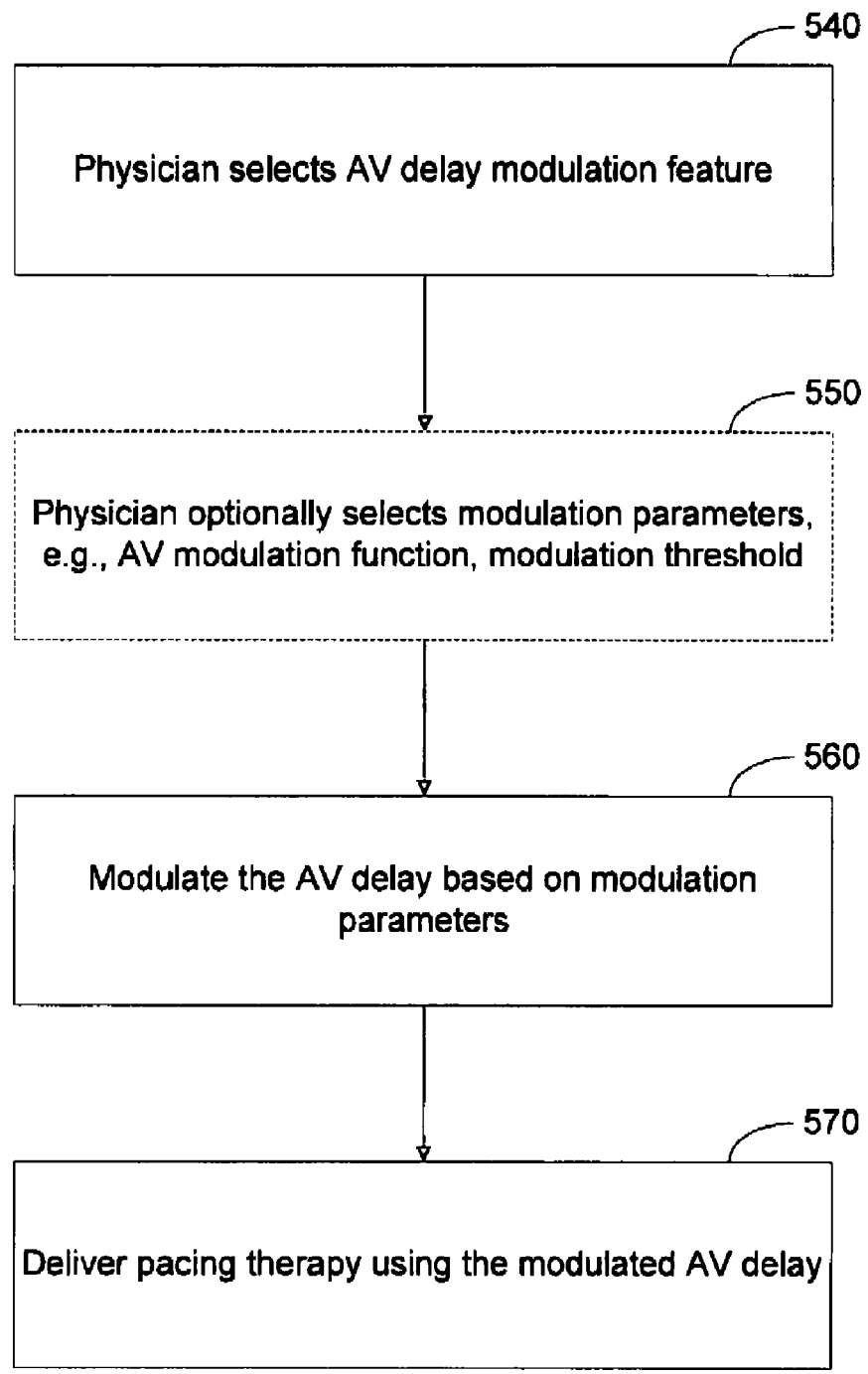
FIG. 5 is a flow diagram of a method for selecting the AV delay modulation feature, the AV delay modulation function, and/or additional AV delay modulation parameters such as range and threshold in accordance with embodiments of the invention.

The AV delay modulation feature may be selected by a physician at the time the CRM device is implanted or at follow-up. The CRM device may provide options for selection of the function used to modulate the base AV delay. The range of modulation and/or the threshold to begin the modulation may also be selected. A method for selecting the AV delay modulation feature and the modulation function and/or additional modulation parameters such as range and threshold is illustrated by the flow diagram of FIG. 5 and the graphs of FIGS. 6A-6C. According to this method, the AV delay modulation feature is selectable 540 by a physician or other human analyst. The physician may optionally select 550 various AV delay modulation parameters, such as the AV delay modulation function with respect to heart rate, the range of modulation, and/or modulation threshold. Selection of the base AV delay function, the AV delay modulation range and the heart rate threshold for beginning AV modulation may depend, for example, on the patient's physical ability, chronotropic condition and/or the patient's intrinsic conduction system including the AV node Through physician selection, these and/or other modulation features may be individualized for each patient based on patient characteristics and/or therapy goals.

Figure 6B:
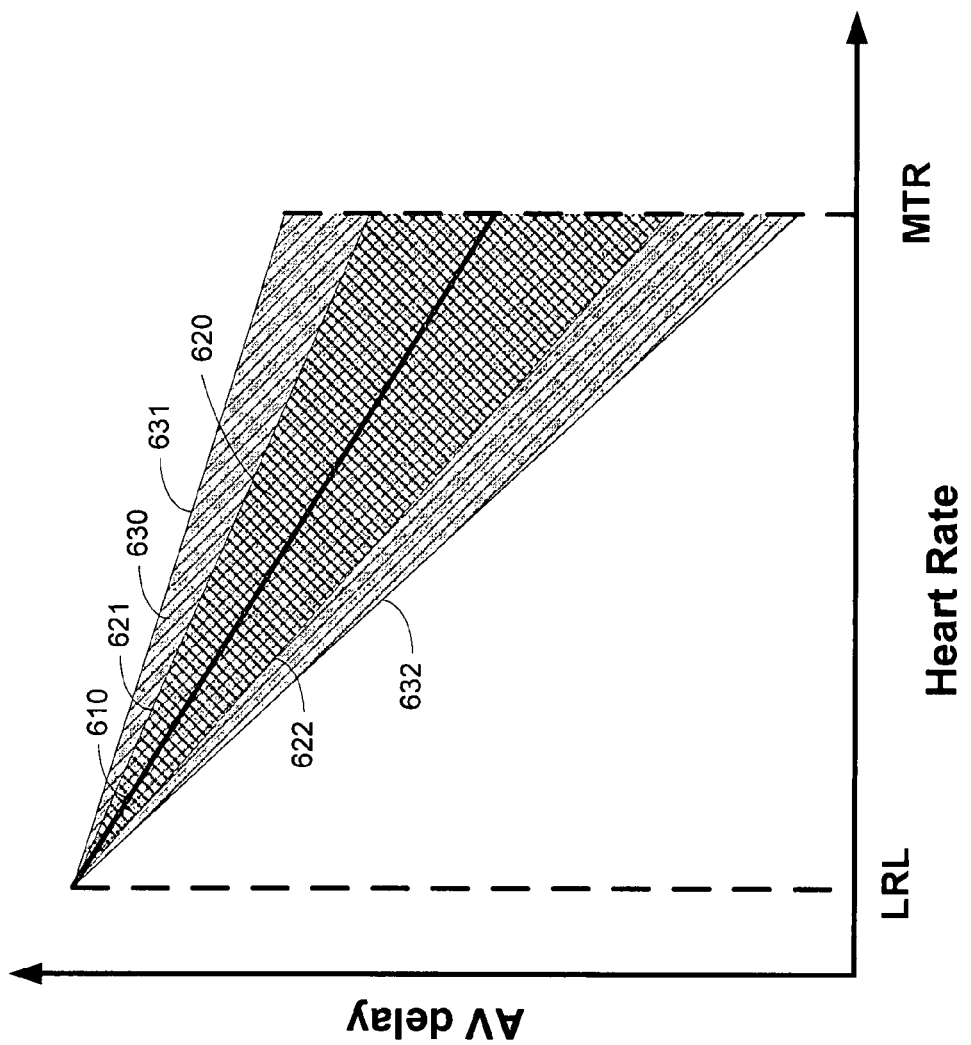
FIGS. 6B and 6C illustrate, respectively, a single base AV delay function and the single base AV delay with three AV delay modulation ranges in accordance with embodiments of the invention.

FIG. 6A illustrates several linear AV delay modulation functions 610-614 that may be selected, each function providing a different slope for AV delay vs. heart rate. In addition to selection of the base AV delay function, various additional modulation parameters, such as modulation range and/or threshold, may be selected. FIG. 6B illustrates a single base AV delay function 610. According to the process outlined in FIG. 5, the physician may select one of several AV delay modulation ranges 620, 630 for the base AV delay 610. For example, the physician may select a modulation range that provides a relatively larger range 630 of AV delay modulation or may select a modulation function that provides a relatively smaller range of AV delay modulation 620. The modulation range may be selected to correspond to the patient's known intrinsic response. The AV delay may have upper and/or can be programmable, so that even with modulation in place, the device is prevented from modifying the AV delay outside the upper and/or lower limits. This is analogous to a maximum tracking rate for tracking modes, but instead of heart rate that has limits, it is the AV delay that has safety limits. Through selection of the AV delay modulation range, the physician can tailor the range of AV delay modulation to providing cardiac cycle timing that is consistent with or enhances the patient's therapy.

In one example, modulation of the AV delay may be accomplished using Equation 1:

$$AV_k = AV_{k-1} - \beta * (AA_k - VV_{k-1}); \quad [1]$$

where $$\beta = \frac{(heartrate - LRL)}{MTR - LRL}$$

In Equation 1 above, $AV_k$ is the AV delay for the current beat; $AV_{k-1}$ is the AV delay for the previous beat; $AA_k$ is the atrial interval for the current beat (e.g., the atrial interval between two consecutive intrinsic atrial beats, between two consecutive paced atrial beats, between a consecutive intrinsic atrial beat and a paced atrial beat or between a consecutive paced atrial beat and an intrinsic atrial beat; $VV_{k-1}$ is the ventricular interval for the previous beat (e.g., the ventricular interval between two consecutive intrinsic ventricular beats, between two consecutive paced ventricular beats, between a consecutive intrinsic ventricular beat and a paced ventricular beat or between a consecutive paced ventricular beat and an intrinsic ventricular beat); and β is the modulation index and is a function of heart rate. The value of β affects the range of AV delay modulation. β may range from about 0 to about 1, where a lower β value produces a smaller AV delay modulation range and a higher β value produces a relatively larger AV delay modulation range.

Figure 6C:
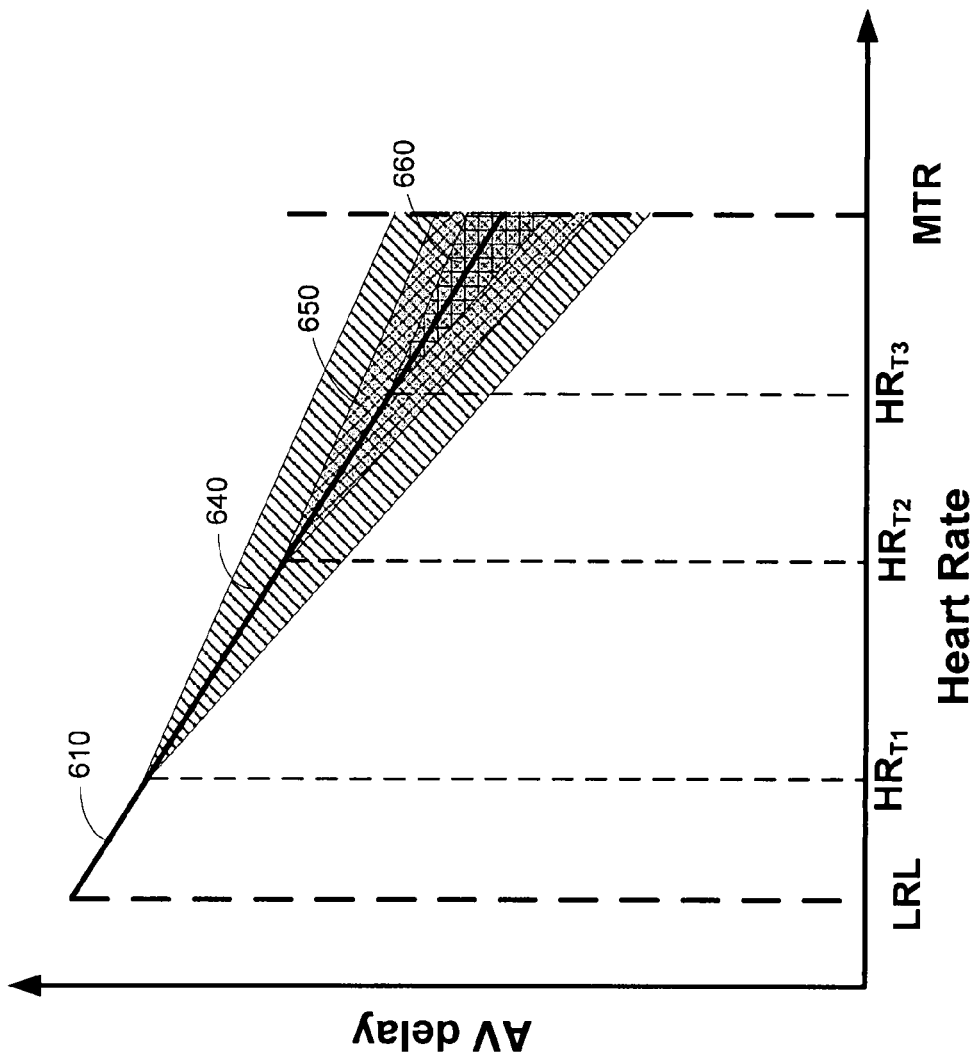

Additionally, or alternatively, the physician may select a heart rate threshold for beginning the modulation of the AV delay. FIG. 6C illustrates a base AV delay function 610 and three AV delay modulation ranges 640, 650, 660. As illustrated in FIG. 6C, for a first modulation range 640, AV delay modulation begins at threshold heart rate $HR_{T1}$, for a second modulation range 650, AV delay modulation begins at threshold heart rate $HR_{T2}$, and for a third modulation range 660, AV delay modulation begins at threshold heart rate $HR_{T3}$.

Figure 7:
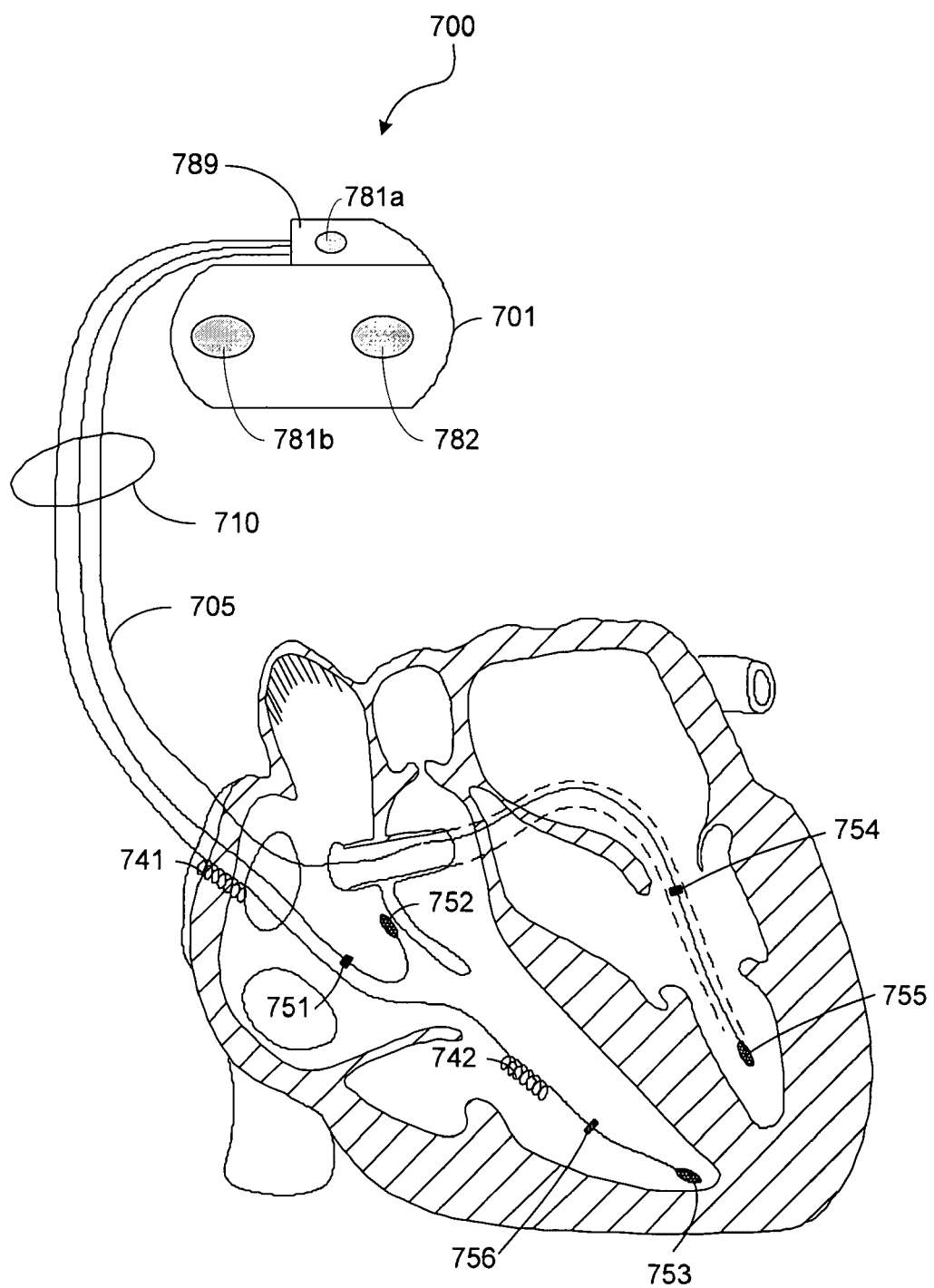
FIG. 7 illustrates a patient-implantable cardiac rhythm management device that may be used to provide therapeutic pacing including AV delay modulation in accordance with embodiments of the present invention.

FIG. 7 shows a cardiac rhythm management (CRM) device 700 that may be used to implement the AV delay modulation techniques discussed in conjunction with the various embodiments. Pacemaker circuitry, having AV delay modulation capability as described herein, is enclosed within an implantable housing 701 and is electrically coupled to an intracardiac lead system 710. Portions of the intracardiac lead system 710 are shown inserted into the patient's heart. The lead system 710 includes cardiac pace/sense electrodes 751-756 positioned in, on, or about one or more heart chambers for sensing electrical signals from the patient's heart and/or delivering pacing pulses to the heart. The intracardiac sense/pace electrodes 751-756 may be used to sense and/or pace one or more chambers of the heart, including the left ventricle, the right ventricle, the left atrium and/or the right atrium. The lead system 710 may include one or more defibrillation electrodes 741, 742 for delivering defibrillation/cardioversion shocks to the heart.

Portions of the housing 701 of the CRM device 700 may optionally serve as one or multiple can or indifferent electrodes. The housing 701 is illustrated as incorporating a header 789 that may be configured to facilitate removable attachment between one or more leads and the housing 701. The housing 701 of the therapy device 700 may include one or more can electrodes 781b. The header 789 of the therapy device 700 may include one or more indifferent electrodes 781a.

The housing 701 and/or header 789 may include one or more sensors 782, such as an accelerometer or microphone. One or more cardiac leads 710 or separate sensor leads may incorporate one or more sensors, producing signals used for detection and/or measurement of various physiological parameters, such as transthoracic impedance, respiration rate, minute ventilation, heart rate, cardiac dyssynchrony, activity, posture, blood chemistry, O2 saturation, heart sounds, wall stress, wall strain, hypertrophy, inter-electrode impedance, electrical delays (PR interval, AV interval, QRS width, etc.), cardiac chamber pressure, cardiac output, temperature, respiration sinus arrhythmia, heart rate variability, depolarization amplitudes, depolarization timing, and/or other physiological parameters. It is contemplated that, in certain embodiments, information derived from such signals may be incorporated into the algorithm that is employed to determine modulated AV delay intervals. The use of physiological signals to control modulation of pacing intervals is described in further detail in commonly owned U.S. patent application Ser. No. 11/799,794, filed May 3, 2007 and incorporated herein by reference.

In some configurations, the CRM device 700 may incorporate one or more transthoracic impedance sensors that can be used to acquire the patient's respiratory waveform, and/or to acquire other respiration-related information. The transthoracic impedance sensor may include, for example, one or more intracardiac electrodes 741, 742, 751-756 positioned in one or more chambers of the heart. The intracardiac electrodes 741, 742, 751-756 may be coupled to impedance drive/sense circuitry positioned within the housing 701 of the therapy device 700. Information from the transthoracic impedance sensor or an activity sensor may be used to determine a sensor indicated pacing rate to correspond to the patient's activity or metabolic need, for example.

Communications circuitry is disposed within the housing 701 for facilitating communication between the CRM system 700 and a patient-external device, such as an external programmer or advanced patient management (APM) system. The communications circuitry may also facilitate unidirectional or bidirectional communication with one or more implanted, external, cutaneous, or subcutaneous physiologic or non-physiologic sensors, patient-input devices and/or information systems.

In certain embodiments, the CRM device 700 may include circuitry for detecting and treating cardiac tachyarrhythmia via defibrillation shocks and/or anti-tachyarrhythmia pacing (ATP). Configurations providing defibrillation capability may make use of defibrillation coils 741, 742 for delivering high energy shocks to the heart to terminate or mitigate tachyarrhythmia.

In some embodiments, the CRM device 700 may additionally include circuitry for selection of pacing electrode(s), timing sequence, and/or amplitude or pulse waveform output configurations (collectively referred to as pacing output configuration) to be applied via one or multiple electrodes within one or multiple heart chambers. The CRM device 700 may include functionality to deliverer non-excitory electrical stimulation via one or more electrodes. In a pacemaker equipped with multiple pacing electrodes respectively disposed at multiple pacing sites within a heart chamber, the ability to select one or more electrodes, temporal sequence, and/or pulse waveform characteristics for delivery of pacing can be used to enhance the contractile function of the heart chamber.

Figure 8:
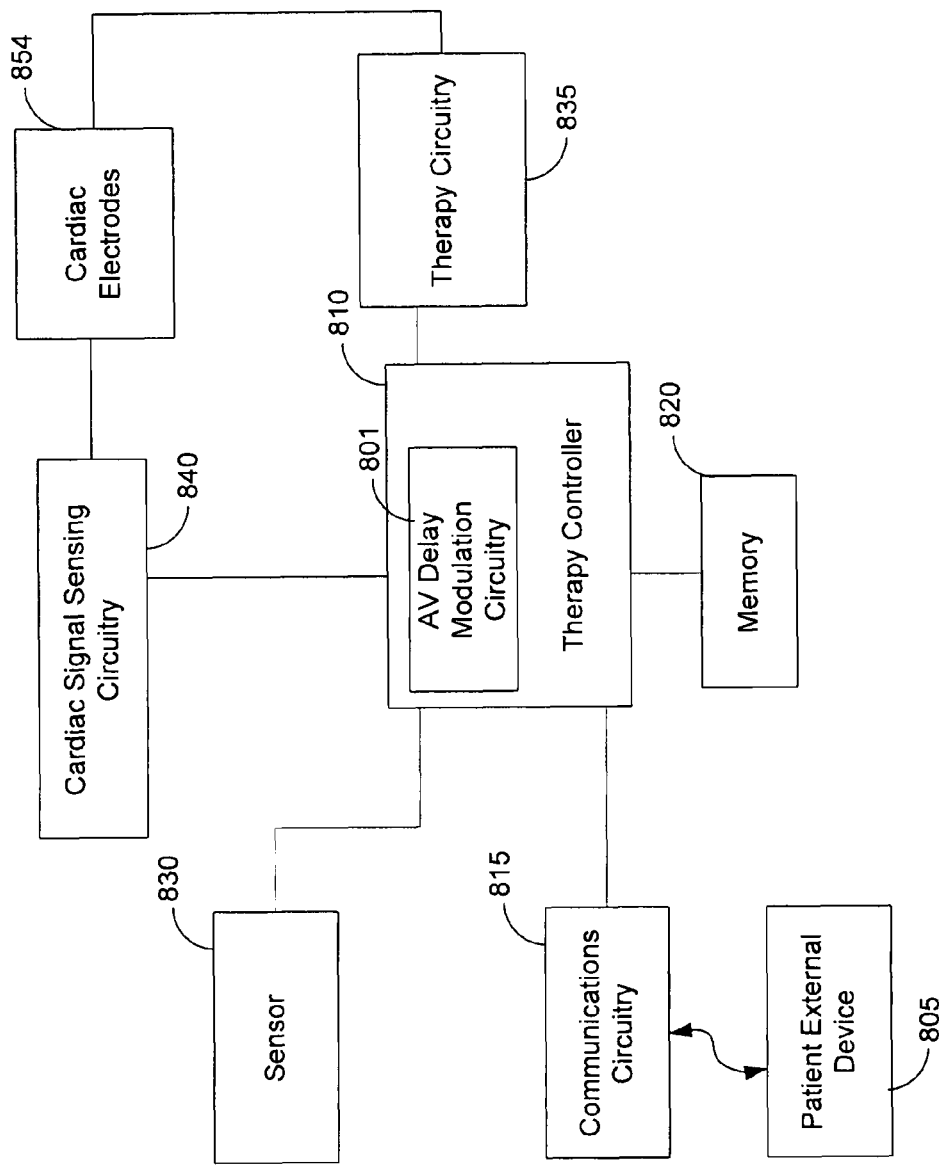
FIG. 8 is a block diagram of circuitry that may be used to implement AV delay interval modulation in accordance with embodiments of the present invention.

FIG. 8 is a block diagram of a CRM device 800 including a therapy controller 810 incorporating AV delay modulation circuitry 801 in accordance with embodiments of the invention. Cardiac electrodes 845 may be positioned at multiple locations within a heart chamber or vasculature. Pace pulses timed to assist the heart in producing a contractile rhythm that maintains cardiac pumping efficiency are delivered via the cardiac electrodes 845 to one or more atria and/or one or more ventricles of the heart. The timing of the pace pulses may involve AV delay modulation determined by the AV delay modulation circuitry 801.

The therapy controller 810 is coupled to memory 820, cardiac signal sensing circuitry 840, therapy circuitry 835, sensors 830 and communications circuitry 815. The memory 820 may store program instructions for execution of algorithms that implement modulation of the AV delay in accordance with embodiments of the invention. AV delay modulation circuitry 801 executes program instructions for operation in conjunction with the therapy controller 810 and therapy circuitry 835 to deliver pacing with AV delay modulation.

Sensors 830 may comprise a minute ventilation sensor or accelerometer configured to sense patient respiration or movement correlated to metabolic demand. Based on the sensor signals, the therapy controller determines a sensor indicated pacing rate that is sufficient to meet the patient's metabolic need.

The memory 820 operating in conjunction with the controller circuitry 810 may provide for collection of data that allows the AV delay modulation parameters to be individualized for a particular patient. For example, the intrinsic AV delay exhibited by a particular patient at various heart rates may be collected and stored in memory. This information can be useful in the selection of the AV delay modulation function, modulation range, and heart rate thresholds. Alternatively, the AV delay modulation parameters may be determined based on clinical population data or a combination of population data and patient-specific data.

In one implementation, the AV delay modulation parameters can be selected to mimic the patient's intrinsic response. In another implementation, cardiac rhythm anomalies experienced by the patient may be detected and/or diagnosed using data collected by the patient. The AV delay modulation parameters may be selected to treat or to correct for the rhythm anomalies. Selection of the AV delay modulation parameters, including the AV delay modulation function, range and/or threshold may be performed automatically by the device or may be performed by a physician. In some implementations, one or more of the AV delay modulation parameters may be selected by a physician based on information provided by the device. In some implementations, one or more of the AV delay modulation parameters may be selected by a physician based on an analysis performed by the device which may include a device recommendation of certain values for the AV delay modulation parameters.

Figure 9:
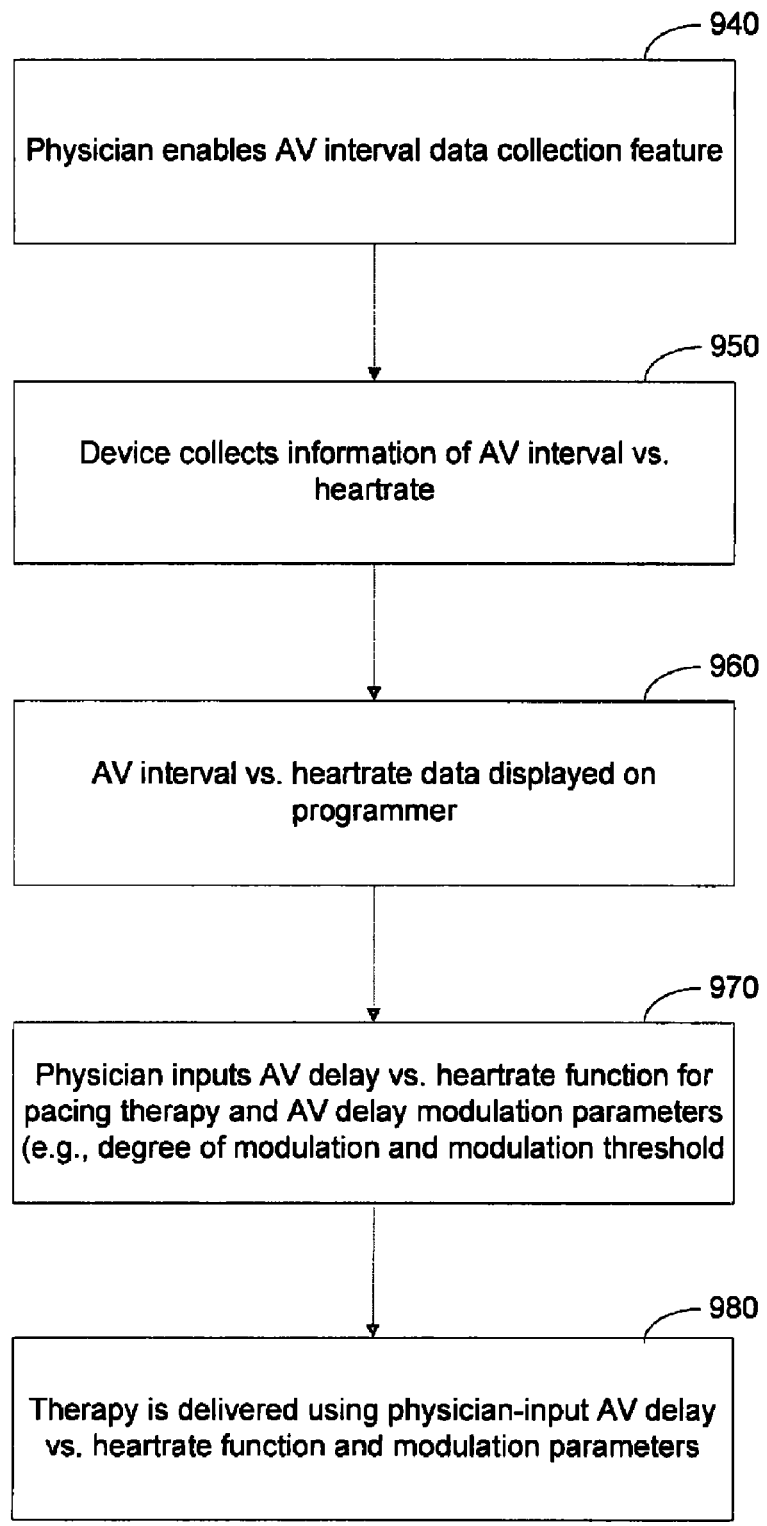
FIG. 9 illustrates a method of selecting AV delay modulation parameters in accordance with embodiments of the invention.

The flow diagram of FIG. 9 illustrates a method of selecting AV delay modulation parameters in accordance with embodiments of the invention. Initially, via the CRM device programmer or other system capable of remotely accessing the CRM device, the physician may select an intrinsic AV interval data collection feature. Selection of this feature causes the device to collect intrinsic AV interval data for a range of heart rates. In one implementation, intrinsic AV interval data collection using this feature may be accomplished in conjunction with a controlled exercise test during which the patient undergoes an exercise protocol designed to induce a desired range of heart rates. In another implementation, the device may automatically sense the patient's heart rate and opportunistically collect intrinsic AV interval data for a range of heart rates as the patient's heart rate varies during day-to-day activities.

Figure 10:
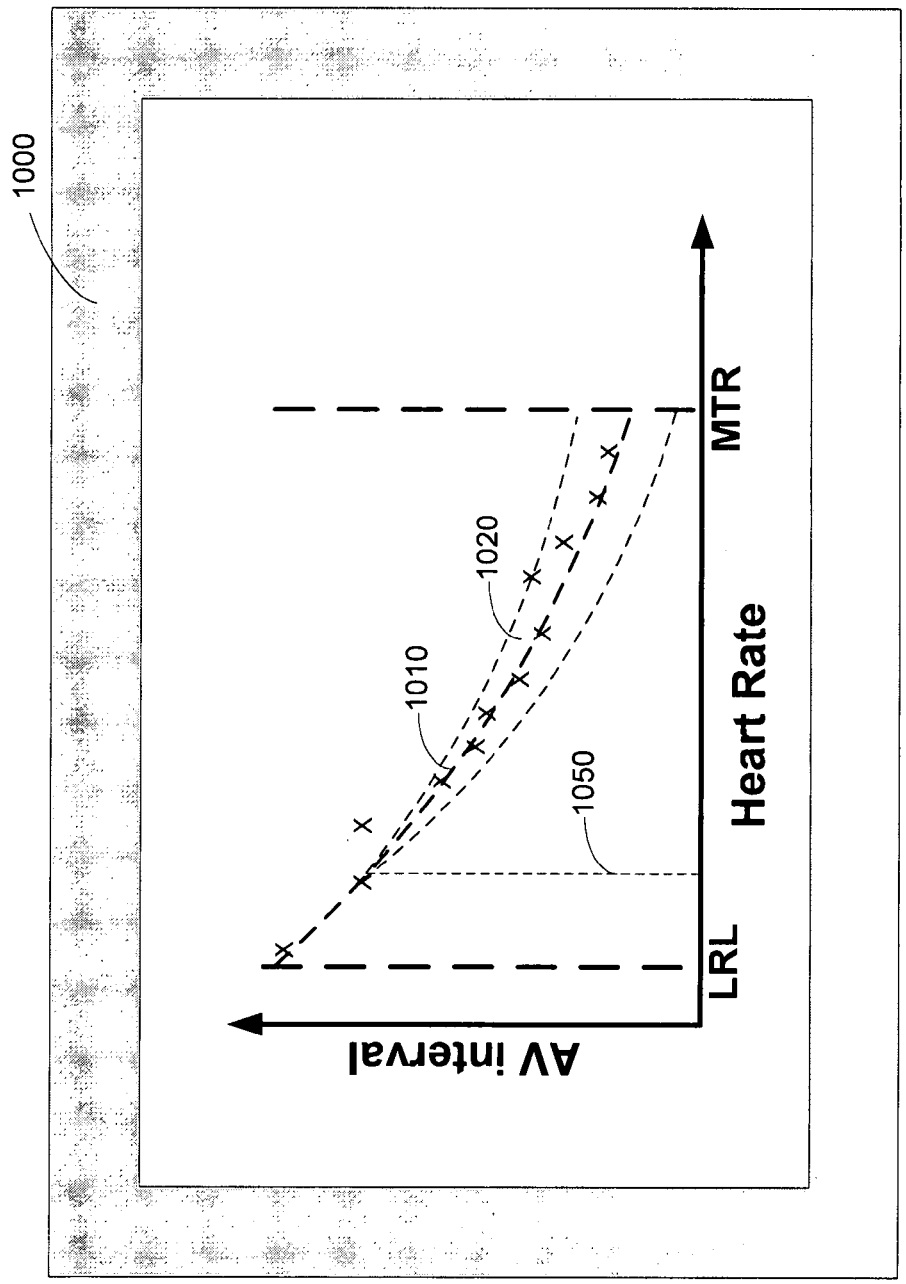
FIG. 10 illustrates a display screen of a programmer or advanced patient management system with data points illustrating collected AV interval data and a process for selection of AV delay modulation parameters in accordance with embodiments of the invention.

Following a period of data collection, the physician interrogates the device via a programmer or remote advanced patient management (APM) server for the collected AV interval data. The programmer or APM server may provide the information to the physician in textual or graphical form. In one embodiment, the collected AV interval data is displayed as a graph of measured AV intervals with respect to heart rate. FIG. 10 illustrates a display screen 1000 of a programmer or APM system with data points (x) illustrating collected AV interval data. As illustrated in FIG. 10, the collected AV interval data may be plotted with respect to heart rates between the LRL and MTR of the CRM device.

After viewing the collected AV interval data, the physician may input a selection for one or more AV delay modulation parameters (e.g., base AV delay function, modulation range or modulation threshold) that provide or enhance the patient's prescribed therapy. For example, physician may select AV delay modulation parameters that mimic the patient's intrinsic response or modulation parameters that correct for cardiac rhythm and/or synchronization defects, or that enhance some other therapeutic goal. As illustrated in FIG. 10, in one implementation, a touch sensitive screen may be used to allow the physician to interact with the programmer or APM device by touching the screen to input a base AV delay function 1010, modulation range 1020, modulation threshold 1050, or other AV delay modulation parameters.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of delivering pacing therapy to a heart, comprising:
   determining a base atrioventricular (AV) delay as a function of heart rate;
   for each cardiac cycle, modulating the base AV delay to reduce beat-to-beat variability of successive ventricular beats, the modulated AV delay compensating for variability of successive atrial beats, wherein modulating the base AV delay comprises varying the AV delay inversely with a change in atrial interval; and
   delivering the pacing therapy using the modulated AV delay.

2. The method of claim 1, wherein determining the base AV delay comprises selecting one base AV delay function from a plurality of possible base AV delay functions.

3. The method of claim 2, further comprising selecting one or more additional AV delay modulation parameters.

4. The method of claim 3, wherein one or both of selecting the base AV delay and selecting the additional AV delay modulation parameters is performed by a human analyst.

5. The method of claim 3, wherein one or both of selecting the base AV delay and selecting the additional AV delay modulation parameters is performed algorithmically by a cardiac device.

6. The method of claim 1, wherein modulating the base AV delay comprises modulating the base AV delay based on an AV delay of a previous cardiac cycle, a ventricular interval of a previous cardiac cycle, and an atrial interval of a current cardiac cycle.

7. The method of claim 1, wherein modulating the base AV delay comprises modulating the base AV delay based on a modulation index, the modulation index associated with a range of AV delay modulation that varies as a function of heart rate.

8. The method of claim 1, wherein modulating the base AV delay comprises modulating the base AV delay after the heart rate exceeds a threshold value.

9. The method of claim 1, further comprising:
   enabling an AV interval data collection mode of a cardiac device;
   collecting, via the cardiac device, data related to a relationship between heart rate and intrinsic AV interval; and
   determining one or more parameters of AV delay modulation using the collected data.

10. The method of claim 9, wherein determining the one or more parameters of AV delay modulation comprises determining the base AV delay based on the collected data.

11. The method of claim 9, wherein determining the one or more parameters of AV delay modulation comprises determining one or both of a modulation index and a threshold for AV delay modulation.

12. A cardiac rhythm management system, comprising:
   electrodes electrically coupled to a heart;
   a therapy controller configured to determine a base atrioventricular (AV) delay as a function of heart rate, and for each cardiac cycle, modulate the base AV delay inversely with a change in atrial interval to reduce beat-to-beat variability in ventricular intervals; and
   a pacing therapy delivery circuit coupled to the pacing controller and the electrodes, the pacing therapy delivery circuit configured to deliver pacing therapy via the electrodes using the modulated AV delay.

13. The system of claim 12, further comprising an external device configured to facilitate selection by a physician of one or more of a base AV delay function and additional AV delay modulation parameters, wherein the therapy controller determines the base AV delay using the selected AV delay function and the additional AV delay modulation parameters.

14. The system of claim 12, wherein the therapy controller is configured to algorithmically select one or more of a base AV delay function and additional AV delay modulation parameters and to determine the base AV delay using the selected AV delay function and the additional AV delay modulation parameters.

15. The system of claim 12, wherein the therapy controller is configured to modulate the base AV delay for the cardiac cycle based on an AV delay of a previous cardiac cycle, a ventricular interval of a previous cardiac cycle, and an atrial interval of the cardiac cycle.

16. The system of claim 12, wherein the therapy controller is configured to collect data related to a relationship between heart rate and intrinsic AV interval and to determine one or more parameters of AV delay modulation using the collected data.

17. A system for delivering pacing therapy to a heart, comprising:
   means for determining a base atrioventricular (AV) delay as a function of heart rate;
   means for modulating the base AV delay for each cardiac cycle to reduce beat-to-beat variability of successive ventricular beats, the modulated AV delay compensating for variability of successive atrial beats, wherein the means for modulating the base AV delay comprises means for varying the AV delay inversely with a change in atrial interval; and
   means for delivering the pacing therapy using the modulated AV delay.

18. The system of claim 17, further comprising means for varying the AV delay inversely with a change in atrial interval.

19. The system of claim 17, further comprising:
   means for enabling an AV interval data collection mode of a cardiac device;
   means for collecting data related to a relationship between heart rate and intrinsic AV interval via the cardiac device; and
   means for determining one or more parameters of AV delay modulation using the collected data.

* * * * *